United States Patent [19]

Wason et al.

[11] 4,045,240
[45] Aug. 30, 1977

[54] AMORPHOUS PRECIPITATED SILICEOUS PIGMENTS AND METHODS FOR THEIR PRODUCTION

[75] Inventors: Satish K. Wason, Havre de Grace; Peter van der Heem, Perryville, both of Md.

[73] Assignee: J. M. Huber Corporation, Locust, N.J.

[21] Appl. No.: 670,018

[22] Filed: Mar. 24, 1976

Related U.S. Application Data

[63] Continuation of Ser. No. 286,656, Sept. 6, 1972, abandoned.

[51] Int. Cl.$^2$ .................. C01B 33/18; C09C 1/28
[52] U.S. Cl. ..................... 106/288 B; 423/339; 423/335
[58] Field of Search ............ 106/288 B, 309; 423/339

[56] References Cited

U.S. PATENT DOCUMENTS

| | | | |
|---|---|---|---|
| 3,235,331 | 2/1966 | Nauroth et al. | 423/339 |
| 3,503,707 | 3/1970 | Burke, Jr. | 106/288 B |

*Primary Examiner*—Patrick P. Garvin
*Assistant Examiner*—J. V. Howard
*Attorney, Agent, or Firm*—Robert L. Price; Harold H. Flanders

[57] ABSTRACT

A method for producing precipitated silicic acid pigments and silicates having a unique combination of physical and chemical properties is disclosed. The pigments are produced by acidulating a solution of an alkali metal silicate with an acid until precipitation just begins. At this point the reaction mass is aged for a period of time and thereafter the acid addition is continued until the precipitated product is obtained. Pigments produced in accordance with the invention exhibit lower wet cake moisture (or higher percent solids).

7 Claims, 2 Drawing Figures

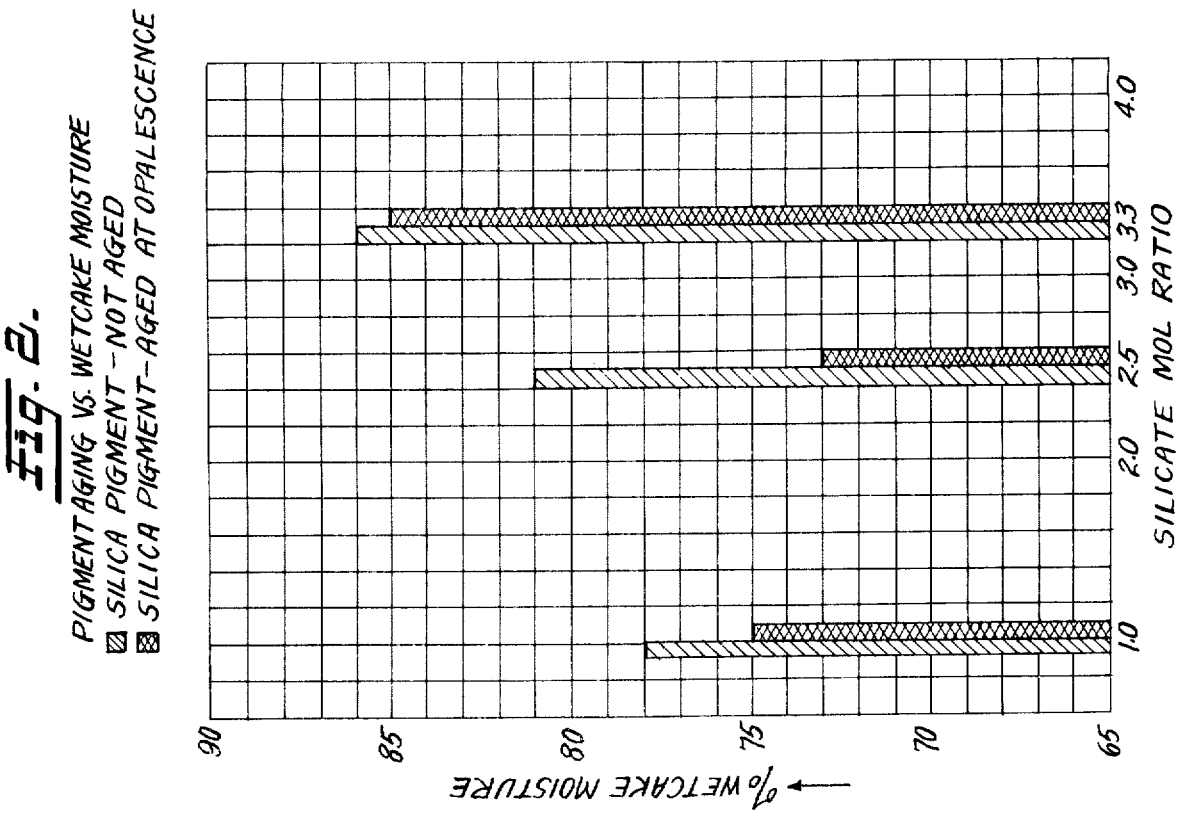
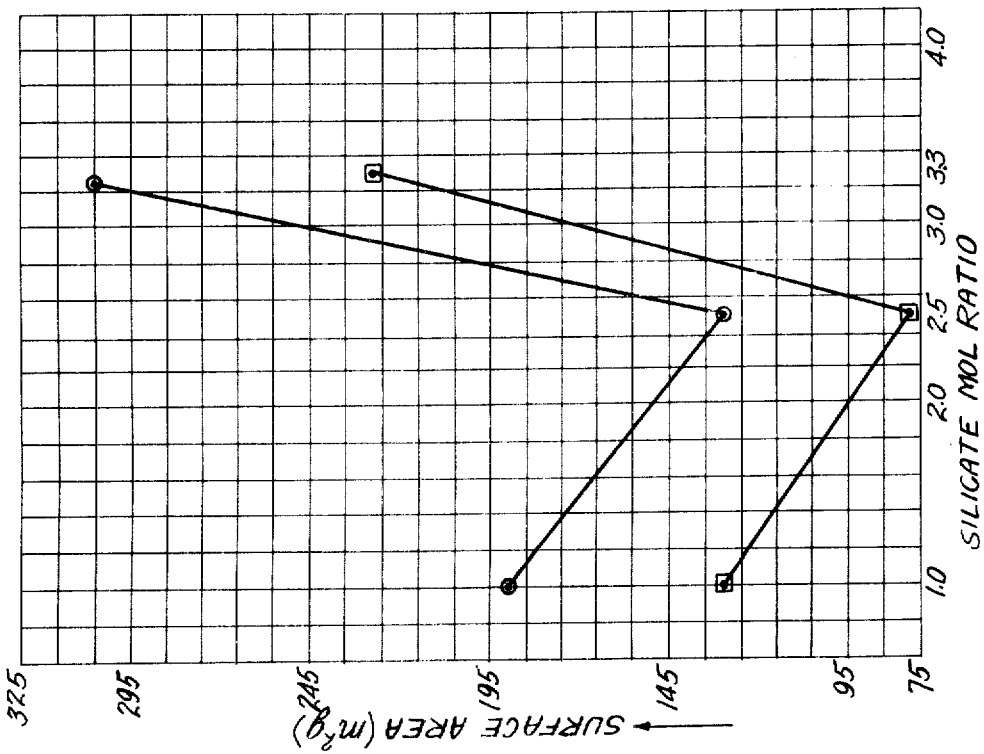

AMORPHOUS PRECIPITATED SILICEOUS PIGMENTS AND METHODS FOR THEIR PRODUCTION

This is a continuation of application Ser. No. 286,656, filed Sept. 6, 1972, now abandoned.

BACKGROUND OF THE INVENTION

1. Field of the Invention

The present invention relates to the production of precipitated silicas and, more particularly, to a novel process for producing synthetic precipitated silicas having new and improved physical and chemical properties.

2. Description of the Prior Art

As known in the art, finely divided amorphous precipitated silicic acid pigments and certain zeolitic type alumino silicates may be prepared by the acidulation of an aqueous silicate solution with an acid or a salt of the acid, such as aluminum sulfate. Such products are commercially available being sold e.g., under the trademarks "Zeo"; "Zeolex" and "Arogen" by the J. M. Huber Corporation. Specific examples of these products as well as methods for their preparation are disclosed in U.S. Pat. Nos. 2,739,073; 2,848,346 and 3,582,379.

While the nature or characteristics of the above discussed precipitated silicic acid (sometimes herein referred to as silicas) and silicate pigments depend, in part, on the chemistry of the silicate solution (specifically the $SiO_2/Na_2O$ ratio of the silicate) as well as the reaction conditions employed (precipitating pH, etc.), prior to the present invention such pigments were characterized by the following properties: high structure, high wet cake moisture content, high oil absorption, low valley abrasion, high surface area and low pack density. In this regard, and due in part to the properties such as high oil absorption, high surface area, etc., the pigments have been widely and successfully used as reinforcing pigments in rubber, in paints, in the manufacture of paper, as moisture conditioners and the like.

However, and generally speaking for the moment, the high wet cake moisture content is disadvantageous in that the drying and filtration rates are decreased thus increasing the overall cost in the production of the final product. For example, in the conventional production of silicic acid pigments as defined above the wet cake moisture content of the product (following filtration of the precipitated reaction mass) is approximately 82%. This means that there can be recovered only 18 parts of dry pigment from 100 parts of wet cake.

SUMMARY OF THE INVENTION

In summary, the present invention relates to the production of synthetic precipitated silicas and silicates having new and improved physical and chemical characteristics. The new products can be advantageously employed in applications such as in the preparation of molecular sieves, as flattening agents, as fillers and carriers and as viscosity control agents.

Stated broadly, the method of the invention embodies the concept and is based on the discovery that if the addition of the acid to the silicate solution is interrupted at the first appearance of the opalescence point (i.e., that point at which precipitation first begins) the resulting pigments possess the aforementioned unique combination of properties. Stated differently, the pigments of the invention are prepared by acidulating the aqueous alkali metal silicate solution (i.e., sodium silicate) until precipitation just begins. At this point the reaction mass is aged for a suitable length of time generally on the order of from about 15 to 20 minutes. After the aging period, the introduction of the acid is continued until the precipitated product is obtained.

As briefly noted above, the precipitated pigments produced in accordance with the invention result in materials of lower processing costs, better packaging characteristics and a unique balance of physical chemical properties as compared to conventionally precipitated silicas.

It is accordingly a general object of the present invention to provide a novel process for producing precipitated silicas having improved physical and chemical properties.

Yet another object is to provide a highly efficient and improved process for producing silicic acid pigment which exhibits lower wet cake moisture or higher percent solids and which have lower oil absorption characteristics.

A further object is to provide a new process for producing precipitated amorphous silicas which have a unique balance of physical and chemical properties as compared to conventionally known precipitated pigments, said process further resulting in lower processing cost.

A still further object is to provide a process for producing low structure, low wet cake moisture, low surface area, low oil absorption, and high pack density precipitated silicic acid pigments.

BRIEF DESCRIPTION OF THE DRAWINGS

The manner in which the foregoing and other objects are achieved in accordance with the present invention will be better understood in view of the following detailed description and accompanying drawings, which form a part of the specification and wherein:

FIG. 1 is a graph showing the effect of the silicate mol ratio on the surface area of pigments produced in accordance with the invention and those produced by prior known techniques.

FIG. 2 is a graph showing the effect of the silicate mol ratio on the wet cake moisture content for pigments produced in accordance with the invention and those produced by prior techniques.

DESCRIPTION OF PREFERRED EMBODIMENTS

As briefly discussed above, when an acid is added to a solution of an alkali metal silicate, the resulting reaction medium remains clear until such point that a slight turbidity (called the opalescence point) appears. As the acid addition is continued, the silicic acid or silica pigment starts precipitating until all of the silicate solution is precipitated. In conventionally known processes, the pH of the reaction mass is then adjusted to a range of from about 5.5 to 6.5 and the mass is filtered, washed and dried.

In accordance with the present invention, it has been discovered that if the acid addition is interrupted for a suitable period of time at the first appearance of opalescence, the resulting pigment possesses a unique combination of physical and chemical properties as well as improved processing advantages. More specifically and again as briefly noted above, the new silicic acid pigments produced in accordance with the invention exhibit lower wet cake moisture (or higher percent solids)

thereby permitting increased drying and filtration rates. Further the new pigments have been found to have low structure, relatively low surface areas, low oil absorption, and high pack densities. Other properties include controlled particle size, better dispersion and improved wetting and viscosity characteristics.

At this point it may be noted that as used herein the term "structure" is intended to include, and is defined as, the ability of a silica or silicate material to hold water in its wet cake. When silicas or silicates, such as the aforementioned conventional precipitated silicas, hold a high percentage of water (i.e., in the neighborhood of 70% to 85%) they are known and referred to as high structure silicas. Materials holding less than 70% and preferably in the neighborhood of from about 50% to 70% water in their wet cake are referred to as low structure silicas.

Turning now to more specific details, in the practice of the invention a solution of the alkali metal silicate is first charged to a reactor and the solution is heated to a temperature in the range of from about 100° F to 200° F, preferably on the order of from about 150° F to 175° F. In general and except as otherwise expressly noted herein, the reaction temperatures and rates as well as the concentration of the reactants, i.e., the silicate solution and acid, are the same as in the above discussed known processes for producing precipitated silicic acid pigments. However, in the practice of the invention it has been found that particularly advantageous results are obtained if the concentration of the silicate solution is on the order of from about 1.0 to about 2.5 pounds/gallon. The acidulating agent or acid, e.g., sulfuric acid, is next charged to the reactor until the slight turbidity (i.e., the opalescent point) first occurs. At this time the acid addition is stopped and the reaction is aged for a period of time on the order of from about 10 minutes to 1 hour. As to be discussed in more detail hereinafter, while the point or time at which the acidulation is discontinued is critical, it has been found that the aging period is generally dictated by process economics. For example, although the reaction mass must be aged for at least 10 minutes to obtain the aforementioned unique combination of properties, it has been found that aging for a period of longer than 2 hours does not, in fact, produce any particular advantage. Therefore from an economic standpoint, the aging period is preferably on the order of from about 10 to 15 minutes.

In the preferred method embodiment, the entire solution of the silicate is initially charged to reactor. After the pigment has been precipitated by the addition of acid, the pH of the resulting slurry is reduced to from about 5.5 to 7.0 by the addition of an excess of the acid.

As will be seen from the above the starting materials or reactants employed in the present invention include alkali metal silicates and an acid. As used herein, the term alkali metal silicates include all the common forms of alkali silicates as, for example, metasilicates, disilicates and water glass. Water soluble potassium silicates and sodium silicates are particularly advantageous. Because of their relatively low cost, sodium silicates are preferred. If employed, sodium silicates are effective in any composition in which the mol ratio of the $SiO_2$ to $Na_2O$ is from about 1 to 4. In this regard commercially available sodium silicate solutions are more or less polymerized depending on their silica to sodium oxide ($SiO_2$/$Na_2O$) ratios. For example, sodium metasilicate solution (mol ratio unity) is known to be predominantly monomeric in character while water glass (mol ratio 3.3) is both monomeric and polymeric in character. As the silica to sodium oxide mol ratio of sodium silicate increases, so does the polymer to monomer ratio of its silicate anions. While sodium silicates having an $SiO_2$/$Na_2O$ mol ratio of from 1 to 4 may be employed, it has been found that particularly advantageous results are obtained if the $SiO_2$/$Na_2O$ ratio is in the range of from about 2.0 to 2.7.

While the acidulating agent or acid is preferably a strong mineral acid, such as sulfuric acid, nitric acid and hydrochloric acid, it should be understood that other acids, including organic acids, as for example, acetic acid, formic, or carbonic acid can be employed.

The acidulating agent or acid is preferably added as a dilute solution thereof. Preferred results are obtained if the acidic solution is from about 10 to 25% by weight acid based on the total weight of the solution. However this may vary depending upon the particular acid employed, etc.

The invention will be further illustrated by the following examples.

EXAMPLE 1

60 gallons of 1.24lbs./gal. sodium silicate solution ($SiO_2$ to $Na_2O$ molar ratio of 2.5) was charged to a stirred reactor and the silicate solution was heated to 180° F. Sulfuric acid of 11.5% concentration was added to the reactor at the rate of 0.87 gallons per minute until a pH of 10.3 was reached. At this pH, the precipitation of silica micelles just started. The acid was shut off and the reaction medium was aged for fifteen minutes. After the aging period, the addition of the acid was continued at the rate of 1.2 gallons per minute and the batch was finished off at pH 5.8, filtered, washed, dried and milled. The results of this and further examples are shown and summarized hereinbelow.

EXAMPLE 2

The procedure of Example 1 was repeated except that after the aging period, the precipitation pH was controlled at pH 9.9 plus or minus 0.1. The batch was finished and processed similar to Example 1.

EXAMPLE 3

The procedure of Example 1 was repeated except that the finishing pH was brought down to 3.2. Lower finishing pH results in product of higher surface area.

EXAMPLE 4

A control batch of conventional precipitated silica was prepared by neutralizing 1.24lbs./gal. sodium silicate with 11.4% acid till the final pH of 5.5 was obtained. In the control batch no aging step was involved so that the properties of material produced via the new process could be compared with the control batch.

Data on precipitated silicas obtained in Examples 1 through 4 are summarized below:

| Example | Description | % Wet Cake Moisture | Surface Area ($m^2$/g) | Oil Absorption cc/100g | Density Pour, pack | Valley Abrasion mg loss |
|---|---|---|---|---|---|---|
| 1 | Silica via aging | 75 | 100 | 170 | 11.2 18.7 | 4.0 |
| 2 | Silica via aging | 74 | 90 | 165 | 12.5 22.2 | 5.0 |
| 3 | Silica via aging | 75 | 200 | 170 | 11.2 18.8 | 4.0 |
| 4 | Control | | | | | |

| Example | Description | % Wet Cake Moisture | Surface Area (m²/g) | Oil Absorption cc/100g | Density Pour, pack | | Valley Abrasion mg loss |
|---|---|---|---|---|---|---|---|
| | (no aging) | 82 | 150 | 211 | 6.3 | 10.7 | 2.5 |

From the above data, it is clear that the new process of the invention results in silicas of lower wet cake moisture, lower structure, lower oil absorption, lower surface area, higher pack density and higher valley abrasion than conventional precipitated silicas.

The new process leads to silicas of lower processing costs than regular precipitated silicas. For example, the average wet cake moisture of silicas via the new process is only 75% as opposed to 82% for regular silica (see control). This means we can recover 25 parts of dry silica from 100 parts of wet cake if the silica is produced via the new process. Regular processes result in recovery of about 18 parts of dry silica per 100 parts of wet cake. Thus, via the new process we can recover 25 parts or 7 parts more dry silica or an increase of (7/18)×100 or 38%. The new process results in silicas of better drying and filtration rates and hence significantly lower processing costs than the precipitated silicas produced by the conventional process.

EXAMPLE 5

In a series of tests the general procedures of Examples 1 - 4 were repeated except that the precipitating pH and the period of aging were varied. The pH was varied in the range of from about 5.5 to 11.0. The aging period was varied from about 5 minutes to 1 hour. The results of these tests were substantially the same as that of Examples 1 - 4 except that it was found that products of predetermined properties and characteristics (i.e., a specific structure or wet cake moisture content) could be obtained by varying the above process conditions within the specified ranges. These tests also established that if the final batch pH was reduced to below about 5.0 an increase in the surface area was obtained. Thus if it is desired that the final product have a low surface area then the pH of the final batch should be maintained above 5.0. Also these tests established that aging for periods of less than about 8 - 10 minutes was generally ineffective to produce the low structures, etc. products of the invention.

EXAMPLE 6

The general procedure of Examples 1 - 5 were repeated except that nitric acid, hydrochloric acid, acetic acid and formic acid were substituted for the sulfuric acid. The results were substantially the same as in Examples 1 - 5.

EXAMPLE 7

In a series of tests the general procedures of Examples 1 - 6 were repeated except that aqueous sodium silicates having mol ratios ($SiO_2/Na_2O$) in the range of from 1 to 4 were substituted for the 2.5 silicate of Examples 1 - 6. The results were substantially the same as above except that it was found that the wet cake moisture content was lower when the 2.5 silicate was employed. In addition the surface area was found to be substantially lower when 2.5 mol ratio silicate was employed. In this regard, in a series of tests the wet cake moisture content and the surface area were compared for silicic acid pigments produced by prior known techniques (non-aged) and products produced in accordance with the present invention. The results are shown in FIGS. 1 and 2.

EXAMPLE 8

In this experiment the determination and variables associated with the first occurrence of the opalescence point as well as the importance of the aging at this point, were investigated. The study revealed that a critical step in producing an acceptable aged pigment is the determination of the opalescence point. For a given batch, the appearance of the opalescence point depends on the following:

Silicate concentration
Silicate mol ratio
Sulfuric acid concentration
Sulfuric acid rate The development work on aged pigment was done by adding 11.4% sulfuric acid at the rate of 450 cc/min to 10 gallons of 2.5 mol ratio silicate of 13.3% concentration. The opalescence point appeared at 21 minutes and 15 seconds of acid addition. When the same batch was prepared with silicate of mol ratio 2.68, the opalescence point appeared at 19 minutes and 30 seconds. The processing advantages of the invention were found to be directly related to the determination of the opalescence point. If the reaction medium is aged by stopping acid about 30 seconds after the appearance of opalescence point, then about 50% of the process advantages are lost. By aging the reaction medium 60 seconds after the opalescence point, 100% of the processing advantages are lost and the product has properties similar to those produced by prior known processes. If the reaction medium is aged after stopping acid about 30 seconds before the opalescence point then an unacceptable product that is slow filtering and which exhibits significant changes in properties is obtained. Thus, an acceptable product can be produced only by stopping the acid addition and aging the reaction medium as soon as the opalescence point appears.

In this regard a Bailey, high range bolometer, was hooked up to the pigment reactor to detect the opalescence point. It was observed that such a sensing device can be used effectively in detecting the opalescence point. It is important that the bolometer chamber be free of air bubbles; otherwise, a false opalescence point will be registered.

The following table (2) is a summary of the results of this study.

TABLE 2

| % W CM | SA (m²/g) | Oil Absorption (cc oil/100g) | M. R. Silicate | Final pH | Remarks* |
|---|---|---|---|---|---|
| 72 | 94 | 147 | 2.61 | 5.9 | 1 |
| 73 | 98 | 141 | 2.68 | 5.9 | 1 |
| 73 | 131 | 153 | 2.68 | 5.6 | 1 |
| 75 | 147 | 161 | 2.68 | 5.5 | 1 |
| 75 | 281 | 134 | 2.68 | 5.5 | 2 |
| 77 | 214 | 165 | 2.68 | 5.5 | 3 |
| 80 | 162 | 182 | 2.68 | 5.4 | 4 |
| 73 | 96 | 141 | 2.5 | — | 1 |
| 71 | 90 | 141 | 2.44 | 5.8 | 1 |

*1 = Aging done by stopping acid at opalescence
2 = Aging done by stopping acid at 60 seconds before opalescence point
3 = Aging done by stopping acid 30 seconds after opalescence point
4 = Aging done by stopping acid 60 seconds after opalescence point

EXAMPLE 9

In further investigations, and following the general procedures of the above examples, a series of tests were conducted in larger reaction vessels. Scale-up proved successful. As predicted from the above examples, aged pigments resulted in an average of about 8% lower wet cake moistures and filtered about three times faster (rotary filter) than products produced by prior known processes. The general chemical-physical properties were the same as those obtained in the smaller reactors.

In still further tests the products produced in accordance with the invention were evaluated for their use in the production of molecular sieves (faujasite) and in paint flatting applications. It was found that the aged products performed significantly better than known products (e.g., "HiSil"®) in faujasite preparations. For example "HiSil"® resulted in a sieve of only about 85% purity while the aged silica pigments of the invention produced sieves of 100% purity.

The following tables summarize the data (average) obtained in these tests.

TABLE 3

|  | ZEO® | AGED SILICA | AGED SILICA | AGED SILICA |
|---|---|---|---|---|
| Acid Rate vs Zeo | Equal | Equal | Equal | Double up to Opal. |
| Aging, 15 minutes at opalescence | No Aging | Yes | Yes | Yes |
| Wet Cake Moisture, % | 82 | 74 | 74 | 75 |
| Filtration rate, dry lbs/hr/ft.$^2$ | 1.5 | 5.3 | 5.8 | 4.5 |
| PHYSICALS |  |  |  |  |
| Surface Area | 114 | 54 | 62 | 60 |
| Oil Absorption, cc/100g | 211 | 173 | 196 | 181 |
| % Moisture | 2.4 | 4.2 | 3.0 | 5.0 |
| % LOI | 4.0 | 3.7 | 3.8 | 3.9 |
| % 325 Residue | 5.0 | 1.1 | 2.3 | 1.3 |
| Valley Abrasion mg wire loss | 2.5 | 5.3 | 5.4 | 5.5 |
| Pour Density, lbs/ft.$^3$ | 6.3 | 7.9 | 7.1 | 7.6 |
| Pack Density, lbs/ft.$^3$ | 10.7 | 10.8 | 13.9 | 15.8 |
| Elrepho Brightness | 95.5 | 98.2 | 97.9 | 97.5 |

TABLE 4

Faujasite Preparation
(In accordance with Ex. XXIII, U.S. Pat. No. 3,130,007)

| Product | % Sieve Purity | $SiO_2/Al_2O_3$ Ratio XRD | $SiO_2/Al_2O_3$ Ratio XRF |
|---|---|---|---|
| HiSil® 233 | 85 | 5.0 | 4.8 |
| Zeofree® 80 | 87 | 4.7 | 4.6 |
| Zeo® | 77 | — | — |
| Aged Silica, Milled | 100 | 4.9 | 4.4 |
| Aged Silica, Milled | 100 | 4.7 | 4.5 |
| Aged Wet Cake | 100 | 4.6 | 4.5 |
| Aged Silica, Spray Dried | 100 | 4.6 | 4.5 |

TABLE 5

| | Flatting Properties | | |
|---|---|---|---|
|  | Zeo® | Zeothix® 95 | Aged Silica |
| Hegman, Grind | 6.5 | 6.0 | 6.0 |
| Dustiness | more | Std. | much less |
| Mixing time, lacquer (minutes) | 3½ | 3 | 1 |
| 60° Gloss |  |  |  |
| 1.75% Pigment loading | 56 | 48 | 46 |
| 3.50% Pigment loading | 41 | 32 | 29 |
| 10.0% Pigment loading | 12 | 8 | 8 |
| 85° Sheen |  |  |  |
| 1.75% Pigment loading | 85 | 80 | 66 |
| 3.50% Pigment loading | 78 | 69 | 49 |
| 10.0% Pigment loading | 50 | 36 | 17 |
| Mar resistance | equal | Std. | Sl. better |
| Clarity | equal | Std. | Sl. less |
| Settling |  |  |  |
| Pour/Pack Density lbs/ft.$^3$ | 2.69/4.25 | 2.77/4.39 | 5.73/10.86 |

CONCLUSIONS: Aged silica pigments (air milled version) possess the following advantages over Zeothix® 95 in flatting application: (1) aged pigments mix faster with lacquer (2) aged pigments are less dusting (3) better in flatting efficiency (4) better in mar resistance (5) significantly cheaper to make (6) possess higher pack density.

From the above it will be seen that the process of the instant invention results in a new product having a unique combination of physical and chemical properties. These include, e.g., lower oil absorption, lower wet cake moisture contents of less than 82%, surface areas of less than 100 m$^2$/g; pack densities of greater than 12 lbs./ft.$^3$ and valley abrasions on the order of 5 (mg. wire loss). Improved and very important processing advantages are also obtained. While particular embodiments have been disclosed for illustrative purposes the invention is not intended to be limited thereto. For example, in the case of pigment production for a special utility the precipitating pH and the final slurry pH may be tailored accordingly. Also, and as should be readily appreciated by those skilled in the art, no special equipment is required in the method herein described. In this regard, however, the reactor should be equipped with heating means, e.g., a steam jacket, in order to maintain the desired reaction temperature and should have adequate agitating means to produce a strong backflow on the body of the liquid and thus avoid zones of high concentration of the incoming reactants. It is desirable to bring the reactants together so as to produce an instantaneous reaction of all material being fed to the fullest extent reasonably possible, as such promotes uniformity of the resulting products. Storage vessels (for the reactants) connected to the reaction vessel thru lines fitted with flow control means may also be provided. The reaction vessel may be equipped with an outlet line leading to a filter which may be of conventional design. As noted above, the filtered mass is washed and dried. Such steps may also be conducted in conventional equipment it being understood, of course, that same do not form a part of the present invention.

What is claimed is:

1. A method for producing amorphous, precipitated silica pigments having an improved combination of chemical and physical properties, said method comprising the steps of: acidulating an aqueous solution of an alkali metal silicate with an acid selected from the group consisting of sulfuric acid, nitric acid, and hydrochloric acid; said alkali metal silicate having a $SiO_2/X_2O$ mol ratio in the range of from about 2.0 to 2.7 wherein X is selected from the group consisting of sodium, potassium, and lithium; said aqueous alkali metal silicate solution having a concentration on the order of about 1.0 to 2.5 pounds silicate per gallon, said acid being added as a dilute solution thereof and having a concentration of from about 10 to 25% by weight acid based on the weight of the solution thereof; continuing the addition of said acid until that point at which precipitation of said pigment just begins; interrupting and discontinuing the addition of said acid to said silicate at said point; aging the aqueous reaction mass for a period of time sufficient to obtain an equilibrium condition of the reactants comprising said reaction mass; continuing the addition of said acid to said aqueous silicate solution following said aging period until the precipitation of said pigment is complete; separating the precipitated pigment from the reaction mass and recovering the product.

2. The method in accordance with claim 1, said method further comprising the steps of separating the precipitated pigment from said aqueous reaction mass and thereafter drying and disintegrating the precipitated material.

3. The method in accordance with claim 1, wherein X is sodium and the acid is sulfuric acid.

4. The method in accordance with claim 1, wherein said alkali metal silicate is selected from the group consisting of sodium silicate, potassium silicate and lithium silicate.

5. The method of claim 1, wherein X is sodium and the $SiO_2/Na_2O$ mol ratio is 2.5.

6. The method in accordance with claim 1, wherein said aging period is in the range of from about 10 minutes to 2 hours.

7. The product produced in accordance with the method of claim 1.

* * * * *